(12) United States Patent
Kim et al.

(10) Patent No.: US 6,337,091 B1
(45) Date of Patent: *Jan. 8, 2002

(54) MATRIX FOR CONTROLLED DELIVERY OF HIGHLY SOLUBLE PHARMACEUTICAL AGENTS

(75) Inventors: Hyunjo Kim, Philadelphia; Reza Fassihi, Ambler, both of PA (US)

(73) Assignee: Temple University - of the Commonwealth System of Higher Education, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/958,470

(22) Filed: Oct. 27, 1997

(51) Int. Cl.⁷ .................................................. A61K 9/26
(52) U.S. Cl. .......................... 424/485; 424/486; 424/488
(58) Field of Search ................................ 424/486, 472, 424/500, 489, 485; 514/774, 782

(56) References Cited

U.S. PATENT DOCUMENTS

| | | |
|---|---|---|
| 3,220,960 A | 11/1965 | Wichterie et al. |
| 3,590,117 A | 6/1971 | Christenson et al. |
| 4,259,314 A | 3/1981 | Lowey |
| 4,309,405 A | 1/1982 | Guley et al. |
| 4,647,396 A | 3/1987 | Denzinger et al. .......... 252/174 |
| 4,666,705 A | 5/1987 | DeCrosta et al. |
| 4,681,755 A | 7/1987 | Colombo et al. |
| 4,786,506 A | 11/1988 | Fontanelli |
| 4,857,331 A * | 8/1989 | Shaw et al. .................. 424/488 |
| 4,956,421 A | 9/1990 | Denzinger et al. .......... 525/385 |
| 4,992,277 A * | 2/1991 | Sangekar et at. ........... 424/488 |
| 5,028,435 A | 7/1991 | Katz et al. |
| 5,069,911 A | 12/1991 | Zuger |
| 5,082,668 A | 1/1992 | Wong et al. |
| 5,128,142 A | 7/1992 | Mulligan et al. |

(List continued on next page.)

FOREIGN PATENT DOCUMENTS

| | | |
|---|---|---|
| EP | 410422 | 1/1991 |
| EP | 587047 | 3/1994 |

OTHER PUBLICATIONS

*J. of Controlled Release*, 29, 1994, pp. 253–267.
*J. of Controlled Release*, 36, 1995, pp. 25–37.
*Chem. Pharm. Bull*, 33, 1985, pp. 4600–4605.

(List continued on next page.)

Primary Examiner—Thurman K. Page
(74) Attorney, Agent, or Firm—Ratner & Prestia

(57) ABSTRACT

The present invention provides a new simple polymeric matrix tablet that delivers highly soluble drugs over long periods of time and is easy to manufacture. More specifically, the drug is first granulated with or encapsulated in a swellable polymer, such as a gum, to form a granule. This granule is disposed in a matrix of a more swellable, erodible polymer, such as HPMC or Polyethyleneoxide, and optionally includes pectin. The more swellable erodible polymer has a diffusion rate coefficient which is greater than the diffusion rate coefficient of the relatively less swellable polymer. It is this difference in diffusion rate coefficients between the first and second polymers which controls the rate of drug release and allows the system to approach zero order drug delivery over the drug release period. Other advantages which the present invention holds over existing systems including ease of manufacturing and reproducibility of release profiles under well defined hydrodynamic conditions. The delivery system of the present invention has a potential to maximally release its drug content in a controlled manner over a long time period while achieving complete dissolution.

10 Claims, 12 Drawing Sheets

U.S. PATENT DOCUMENTS

| | | | |
|---|---|---|---|
| 5,175,361 A | | 12/1992 | Denzinger et al. .......... 562/590 |
| 5,178,868 A | | 1/1993 | Malmqvist-Granlund et al. |
| 5,232,704 A | | 8/1993 | Franz et al. |
| 5,252,337 A | | 10/1993 | Powell |
| 5,393,765 A | | 2/1995 | Infeld et al. |
| 5,445,826 A | | 8/1995 | Kuhrts |
| 5,445,829 A | | 8/1995 | Paradissis et al. |
| 5,472,710 A | * | 12/1995 | Klokkers-Bethke et al. 424/470 |
| 5,478,574 A | | 12/1995 | Baichwal et al. |
| 5,514,670 A | | 5/1996 | Friedman et al. |
| 5,529,790 A | * | 6/1996 | Eichel et al. ............... 424/472 |
| 5,549,913 A | * | 8/1996 | Columbo et al. .......... 424/472 |
| 5,554,387 A | | 9/1996 | Baichwal |
| 5,558,880 A | * | 9/1996 | Gole et al. .................. 424/488 |
| 5,593,694 A | | 1/1997 | Hayashida et al. |
| 5,594,091 A | | 1/1997 | Igari et al. |
| 5,783,212 A | * | 7/1998 | Fassihi et al. .............. 424/472 |

OTHER PUBLICATIONS

*J. of Cell Biol.*, 87, 1980, pp. 736–744.

*Int. J. of Pharm.*, 99, 1993, pp. 229–238.

*J. of Controlled Release*, 29, 1994, pp. 329–338.

Naggar et al.; Pectin, a possible matrix for oral sustained–release preparations of water–soluble drugs; S.T.P. Pharma. Science, 1992.

Ju et al.; A Mechanistic Model for Drug Release from Hydrophilic Matrices Based on the Structure of Swollen Matrices; Proceed. Intern. Symp. Control. Rel. Bioact. Mater., 22 (1995), Controlled Release.

Lindner et al.; Drug Release from Hydrocolloid Embeddings with High or Low Sysceptibility to Hydrodynamic Stress; Pharmaceutical Research, vol. 12, No. 11, 1995.

Colombo et al.; Drug Diffusion Front Movement is Important in Drug Release Control from Swellable Matrix Tablets; Journal of Pharmaceutical Sciences; vol. 84, No. 8, Aug. 1995.

Yamakita et al.; Preparation of Controlled Release Granules of TA–5707F Using Enteric Polymers and Ethylcellulose, and Their in Vivo Evaluation; Biol. Pharm. Bull. 19(1) 106 113 (1996).

Kim et al.; Application of a Binary Polymer System in Drug Release Modulation. 1. Characterization of Release Mechanism; Journal of Pharmaceutical in Advance ACS Abstracts, Feb. 1, 1997.

Kim et al.; Application of a Binary Polymer System in Drug Release Modulation. 2. Influence of Formulation Variables and Hydrodynamic Conditions in Release Kinetics; Journ. of Pharm. in Advance.

* cited by examiner

Comparison of diltiazem hydrochloride release from Dilacor™ XR and the designed ternary polymeric hydrophilic matrix tablets produced at 2000 lb

MATRIX FOR CONTROLLED DELIVERY OF HIGHLY SOLUBLE PHARMACEUTICAL AGENTS

BACKGROUND OF THE INVENTION

Controlled release pharmaceutical dosage forms have received much attention in recent years and are highly desirable for providing a constant level of pharmaceutical agent to a patient. The use of single or multiple unit dosage forms as controlled drug delivery devices encompasses a wide range of technologies and includes polymeric as well as nonpolymeric excipients. These dosage forms optimize the drug input rate into the systemic circulation, improve patient compliance, minimize side effects, and maximize drug product efficacy.

The use of controlled release products is frequently necessary for chronic drug administration, such as the use of the calcium-channel blockers nifedipine, diltiazem and verapamil in the management of angina and hypertension. Worldwide sales of these drugs exceeds eight billion dollars. For delivery system design, physiochemical properties and intrinsic characteristics of the drug, such as high or low solubility, limited adsorption, or presystemic metabolism, may impose specific constraints during product development.

Advancements of extended release drug products have come about by the simultaneous convergence of many factors, including the discovery of novel polymers, formulation optimization, better understanding of physiological and pathological constraints, prohibitive cost of developing new drug entities, and the introduction of biopharmaceutics in drug product design.

One aspect of research about controlled-release delivery systems involves designing a system which produces steady-state plasma drug levels, which is also referred to as zero-order drug release kinetics. To meet this objective, numerous design variations have been attempted, and their major controlling mechanisms include diffusion/dissolution, chemical reactions, osmosis, erosion, and swelling.

One attractive design for potential zero-order drug release is hydrophilic swellable matrices with various geometrical modifications. Drug diffusion from the matrix is accomplished by swelling, dissolution and/or erosion. The major component of these systems is a hydrophilic polymer. In general, diffusivity is high in polymers containing flexible chains and low in crystalline polymers. With changes in morphological characteristics, the mobility of the polymer segments will change and diffusivity can be controlled. Addition of other components, such as a drug, another polymer, soluble or insoluble fillers, or solvent, can alter the intermolecular forces, free volume, glass transition temperature, and consequently, can alter the transport mechanisms.

For controlled-drug delivery from hydrophilic matrices, noncross-linked polymers (i.e., in dry form, glassy state), such as hydroxypropyl methylcellulose (HPMC), carboxymethylcellulose, polyvinyl alcohol, or polyethylene oxide, with dispersed drugs in them are often tabletted to achieve simple matrix systems. Depending on the system modifications, various drug release rates and patterns can be accomplished. The swelling mechanisms and kinetics of drug release from these systems are highly complex. In general, when such systems are exposed to dissolution media, drug delivery is governed by two distinctive processes; namely, matrix swelling and dissolution/erosion at the matrix periphery. The initial swelling (i.e., the transition of glassy structure to rubbery state) occurs at a rate that is mainly a function of matrix composition and dissolution medium penetration into the matrix. At some point, front synchronization between the dissolution medium/swollen front and the rubbery/glassy front may occur, after which the drug release could be linear. However, it is reported that linear drug release is also achievable in the absence of front synchronization. The final changes in release rates are associated with the degree of polymer disentanglements and/or dissolution/erosion. The release mechanism operates via polymer relaxation (swelling) and drug diffusion/system erosion, and has been described by the following equation:

$$\frac{Mt}{M_\infty} = at^{1/2} + \gamma t \qquad (1)$$

where amount of drug released, $Mt/M\infty$, is the sum of a diffusional contribution (with $t^{1/2}$ dependence) and a relaxational contribution (with t dependence), and both $\alpha$ and $\gamma$ are constants describing the diffusion-controlled release mechanism and constant rate process, respectively. However, when gel layer thickness is constant (i.e. at front synchronization), the amount of drug released can been expressed as follows:

$$\frac{Mt}{M_\infty} = \xi + \epsilon t \qquad (2)$$

where the contribution of the $t^{1/2}$ term coefficient of equation 1 becomes negligible. More detailed mathematical treatment of drug/polymer matrix swelling and dissolution can be found in the literature. Under conditions where drug release and swelling is not limited to planar geometry, as usually is the case with simple hydrophilic matrix tablets, the exact analysis will be complicated, especially when more than one polymer is incorporated into the matrix. Even so, release profiles and mechanisms can be interpreted and explained according to the principles upon which equations 1 and 2 are based.

To date, many studies have investigated drug release from hydrophilic matrix tablets containing a single polymer, a mixture of synthetic polymers, synthetic and natural gelling agents with an optional cationic cross-linking agent, and polysaccharides and gums capable of cross-linking.

Diltiazem is a benzothiazepine derivative with active metabolites. Its oral adsorption is greater than 90%, its bioavailability ranges from 30 to 60% due to extensive variable first-pass metabolism, and its elimination half-life is 3–6 hours. The protein binding is greater than 90% and it has a high clearance from plasma. The water solubility of diltiazem exceeds 50%. Daily doses of 120 to 360 mg are usually used for angina and hypertension. The drug was approved by the FDA in 1988, and is currently available as once-a-day dosage forms.

Current methods of production of Diltiazem are both complicated and cumbersome. A once-a-day, extended-release diltiazem tablet which consists of a simple matrix and which can be manufactured with high-speed tableting machines will represent a significant advance. Such a matrix could also be used to deliver other highly soluble drugs.

In the past, many controlled-release systems for low or sparingly soluble drugs have been developed, but considerable difficulties have been experienced in the formulation of highly ionized and soluble drugs, such as diltiazem or propranolol especially at relatively high doses (e.g., >100 mg).

SUMMARY OF THE INVENTION

The present invention is directed to a new monolithic tablet that delivers highly soluble drugs at a relatively constant release rate over extended periods of time, typically 16 to 20 hours, and that is easy to manufacture. The monolithic tablet which approaches zero order delivery of highly soluble drugs is comprised of a drug incorporated first in relatively less swellable polymer granules and secondly in a more swellable, erodible polymer matrix surrounding the granules. The relatively less swellable polymer granules have a first diffusion rate coefficient, and the more swellable, erodible polymer matrix has a second diffusion rate coefficient which is greater than the diffusion rate than that of the granules. The incorporation of the drug in the first polymer can consist either of granulating the drug with or encapsulating the drug in the first polymer. The first polymer may be a gum, such as gelatin, gum tragacanth, or pectin. The second polymer is composed of HPMC or polyethyleneoxide, and optionally includes pectin. The highly soluble drug may be diltiazem or propranolol. In a preferred embodiment, the second polymer is composed of HPMC and pectin, and the range of pectin:HPMC ratios is from 2:7 to 4:5 by weight in the matrix.

GLOSSARY

The following illustrative explanations are provided to facilitate understanding of certain terms used frequently herein. The explanations are provided as a convenience and are not meant to limit the invention.

Diltiazem is a benzothiazepine derivative and a calcium antagonist used to treat chronic heart disease, such as angina pectoris, myocardial ischaemia, and hypertension.

A "gum" is a carbohydrate-containing polymer composed of monosaccharide units joined by glycosidic bonds, that is insoluble in alcohol and other organic solvents, but generally soluble or dispersible in water. A gum may also be defined as a hydrophilic polysaccharide or derivative that swells to produce a viscous dispersion or solution when added to water. By still another definition, gums have no common structure but are polysaccharides containing several sugars with alternating monomer structures and may or may not contain uronic acids. Viscous-forming polymers typically are gums, but can also include synthetic polymers with similar physical properties. Typical gums used for the present invention can include but are not limited to, guar gum, gum arabic, gum karaya, gum ghatti, locust bean gum, tamarind gum, agar, carageenan gum, pectin and gluten.

Gum arabic refers to an acidic polymer of galactose and rhamnose and is a water-soluble gum that is obtained from acacia trees and produced commercially as a white powder.

Pectin or a pectic substance generally refers to a high molecular weight hydrocolloidal substance (or polyuronide) related to carbohydrates and consisting chiefly of partially methoxylated polygalacturonic acids joined in long chains containing arabinose, galactose, xylose, and rhamnose.

"Granulation" refers to the process of reducing a material to grains or bringing small particles, together with the aid of a gum, binder, or viscous agents.

DETAILED DESCRIPTION OF THE INVENTION

Figure 1A:
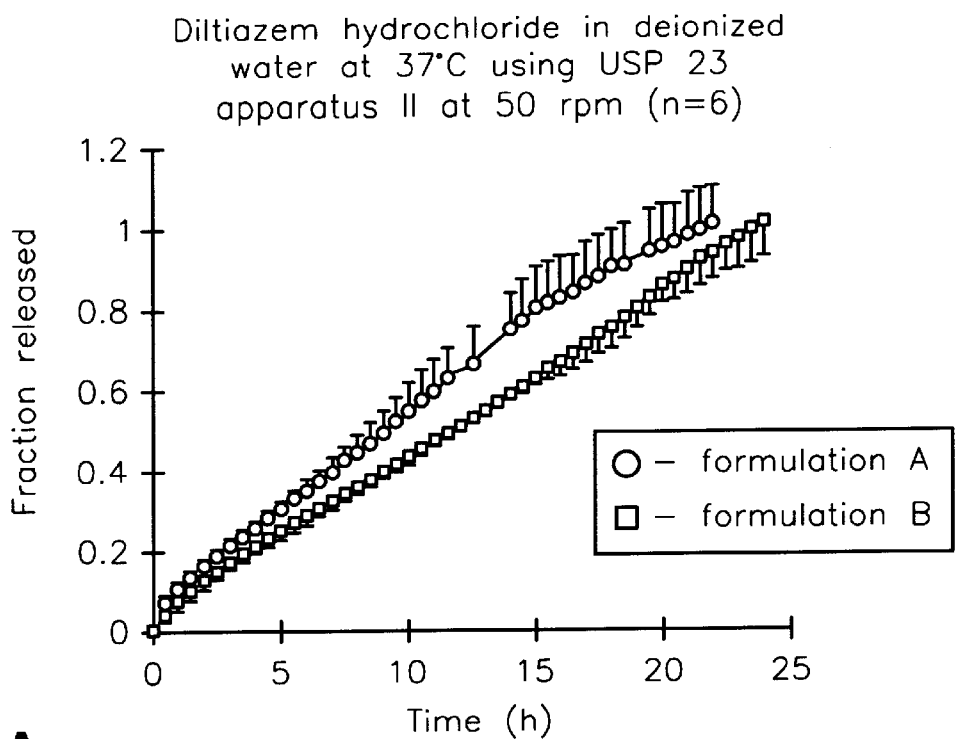
FIG. 1a is a graph showing the fraction release profile of diltiazem hydrochloride from the tablets in accordance with example 1 of the present invention and formulation A and B of Table 1.

The present invention provides a new simple polymeric matrix tablet that delivers highly soluble drugs over long periods of time. More specifically, the drug is first granulated with or encapsulated in a less swellable polymer, such as a gum, to form a granule. This granule is disposed in a matrix of a more swellable, erodible polymer. The more swellable erodible polymer has a diffusion rate coefficient which is greater than the diffusion rate coefficient of the relatively less swellable polymer. Averaged over the entire period of drug release, the diffusion rate for the more swellable polymer is greater than the diffusion rate for the less swellable polymer. It is this general difference in rates of diffusion between the first and second polymers which controls the rate of drug release and allows the system to approach zero order drug delivery over the drug release period.

This new design of a simple matrix tablet consists, in its preferred embodiment of pectin:HPMC (in ratios between 2:7 and 4:5) as the more swellable polymer, and gelatin as the less swellable polymer for the controlled delivery of highly soluble drugs such as diltiazem hydrochloride or propranolol. According to this preferred embodiment, diltiazem HCl (or some other drug such as propranolol), is granulated with gelatin or gum, such as tragacanth, or pectin, and is then surrounded by a matrix of hydroxypropylmethylcellulose (HPMC) or polyethyleneoxide (and optionally including pectin at optimized ratios) and are blended at different loading doses and directly compressed into tablet matrices of different weights. This polymeric matrix system is suitable for controlled release of highly soluble drugs and offers a number of advantages over existing systems including ease of manufacturing and release modulation, as well as reproducibility of release profiles under well defined hydrodynamic conditions. The delivery system of the present invention has a potential to maximally release its drug content in a controlled manner over a long time period while also achieving complete dissolution.

EXAMPLES

Diltiazem hydrochloride and propranolol were obtained from Sigma Chemicals (St. Louis, Mo.). Granular gelatin type A was obtained from AMEND Drug and Chemical Co. (Irvington, N.J.). Pectin type 621, which is designated as high methoxylated pectin citrus with a degree of methoxylation of 65–72%, was obtained from Pectagel Co. (Great Neck, N.Y.). Hydroxypropylmethylcellulose (HPMC) 2208 was supplied by Dow Chemicals (Midland, Mich.) as METHOCEL, K4M having nominal viscosity of 4,000 cps in water at 2% w/v level. Polyethylene oxide (PEO) was supplied by Union Carbide Co. (Danbury, Conn.) as Polyox-WSR 301 (water soluble resin) having molecular weight of $4 \times 10^6$. Tragacanth and magnesium sterate (AMEND Drug and Chemical Co., Irvington, N.J.) were used. All other chemicals were of reagent grade.

The following examples are included to more clearly demonstrate the overall nature of the invention. The examples are exemplary, not restrictive, of the invention. Compositions of the Examples are set forth in Table 1 below:

TABLE 1

| | Ingredients (mg) | | | | | |
|---|---|---|---|---|---|---|
| Formulation | Diltiazem hydrochloride | Gelatin Type A | HPMC K4M | Pectin High methoxylated) | MG stearate | Total tablet weight (mg) |
| A | 140 | 140 | 90 | 45 | 5 | 420 |
| B | 200 | 200 | 194 | — | 6 | 600 |
| C | 100 | 100 | 196 | 98 | 6 | 500 |
| D* | 70 | | 226 | — | 4 | 300 |
| E | 200 | 200 | 116 | 29 | 5 | 550 |
| F | 200 | 299 | 145 | — | 5 | 550 |

*Negative control

EXAMPLE 1

Granulation

Required quantities of drugs and less swellable polymer were sieved through a 40 mesh screen and blended in a cube mixer for 10 minutes. The ratio of drug to less swellable polymers, such as gelatin Type A, in this example was 1:1 unless stated otherwise. The powder blend was transferred into a mortar and ethanol was gradually added as a granulating agent with continuous mixing. The wet homogeneous mass was dried overnight in an air convection type oven at 30° C. The dried mass was sieved through a #20 mesh US-standard sieve and stored in an air-tight container for further use.

Tablet Preparation

Tablets containing equivalent of 10, 20, and 23% (w/w) various drag powder and granules (using each drug and less swellable polymers in the ratio of 1:1) were blended together with more swellable polymers (HPMC or PEO) or pectin:HPMC (3:6) mixture and directly compressed with a carver press (Model C, FRED S. Carver Inc. 1569 Morris St. Wabash, Ind.) using 11 mm flat-faced-punch and die. Powder mixtures were blended in a cube mixer for 10–15 minutes. Then, 1% (w/w) magnesium stearate was added to all formulations, and the formulations were mixed for an additional 5 min prior to compression. Tablets were produced at 2000 pounds in a standard tablet forming press to give tablet hardness values of 10 Kp as determined by laboratory hardness tester (Erweka hardness tester, model 2E, Schleuniger, Zurich, Switzerland). Each tablet weighed 300, 350 and 500 mg, as is needed.

Dissolution Studies

Representative samples from each tablet batch were subjected to dissolution study using 900 mL of deionized water 37° C. and 50 rpm with the USP 23 dissolution apparatus II (paddle method) for diltiazem hydrochloride. The system was automated using an HP diode array UV spectrophotometer, 8452a with continuous sampling, using a peristaltic pump (HP flow control, 89092A) and Mckinet software (HP 89532K Multicell Kinetics Software) for data analysis. Measurements were performed at 238 nm. Controlled-dissolution experiments showed that there was no interference in the UV absorption due to the dissolved pectin, gelatin, HPMC, or their combinations. Fresh dissolution medium (5 mL), heated to 37° C., was added to the vessel to maintain constant volume. Each experimental ran (n=3) was done at least in duplicate. In addition, HPLC analysis of diltiazem samples (USP 23 method) confirmed that there was no degradation product for the entire dissolution period. The results of these experiments are described below.

EXAMPLE 2

Tablets were also prepared according to the composition in Example 1, but in this case, propranolol was substituted for diltiazem. The dissolution study was performed in 1,000 ml deionized water at 37° C. and 100 rpm. Measurements were performed at wavelength 289 nm. Experimental results are described below.

Experimental Results

Figure 1B:
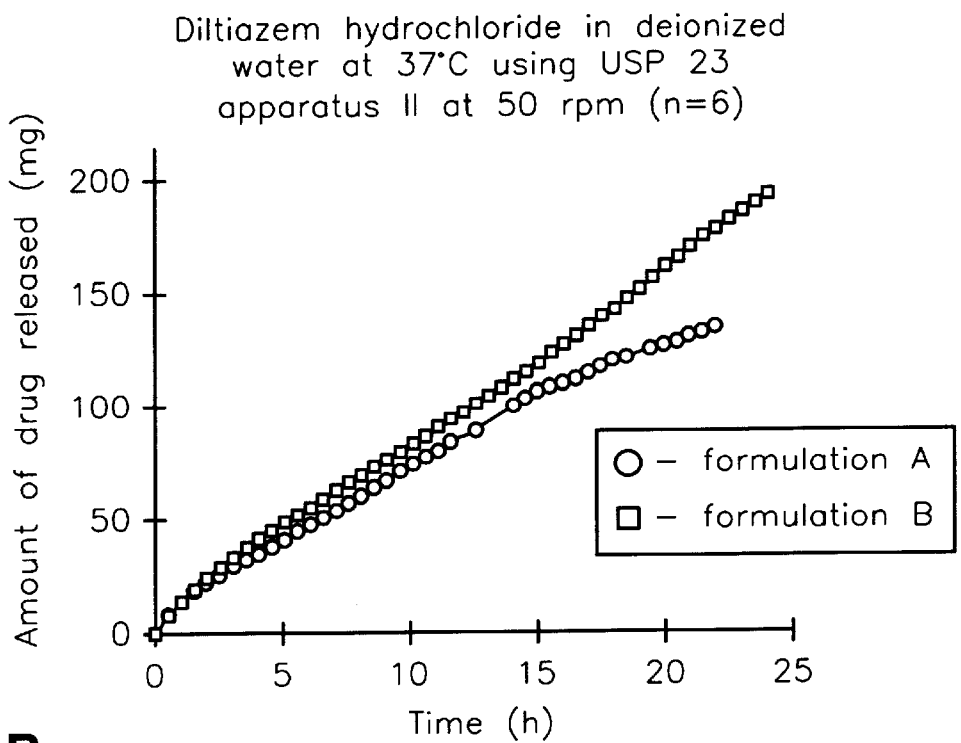
FIG. 1b is a graph showing the amount of diltiazem hydrochloride release from the tablets in accordance with example 1 of the present invention and formulation A and B of Table 1.

FIG. 1 shows the dissolution profile of diltiazem hydrochloride in deionized water for formulations A and B of Table 1. The overall fraction released is shown in FIG. 1a, and the actual amount release (in milligrams) is depicted in FIG. 1b. As can be seen from FIG. 1, the diltiazem release from the tablets made according to the present invention was nearly constant over a 16 hour period. Such release rates are virtually zero-order and highly desirable for extended release tablets.

Figure 2A:
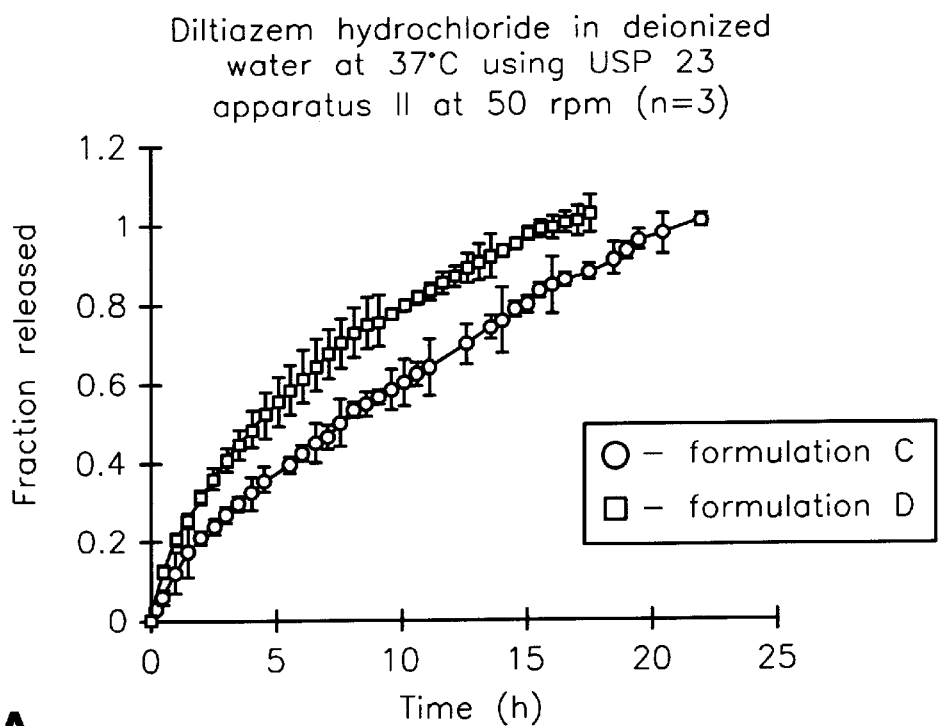
FIG. 2a is a graph showing the fraction release of diltiazem hydrochloride from the tablets in accordance with example 1 of the present invention and formulation C and D of Table 1.
Figure 2B:
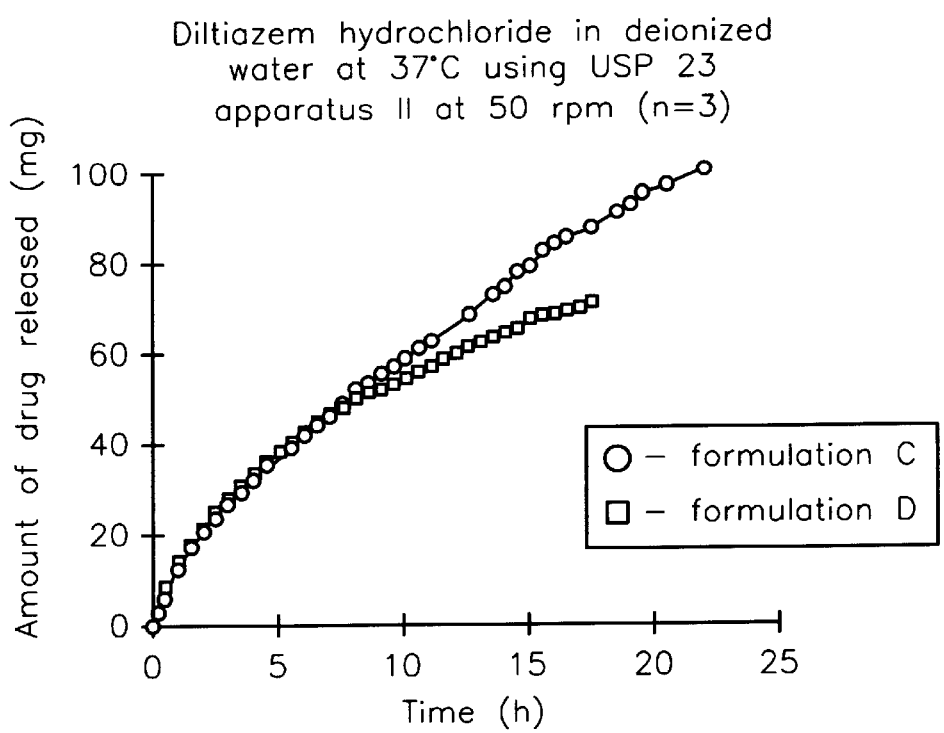
FIG. 2b is a graph showing the amount of diltiazem hydrochloride release from the tablets in accordance with example 1 of the present invention and formulation C and D of Table 1.
Figure 3A:
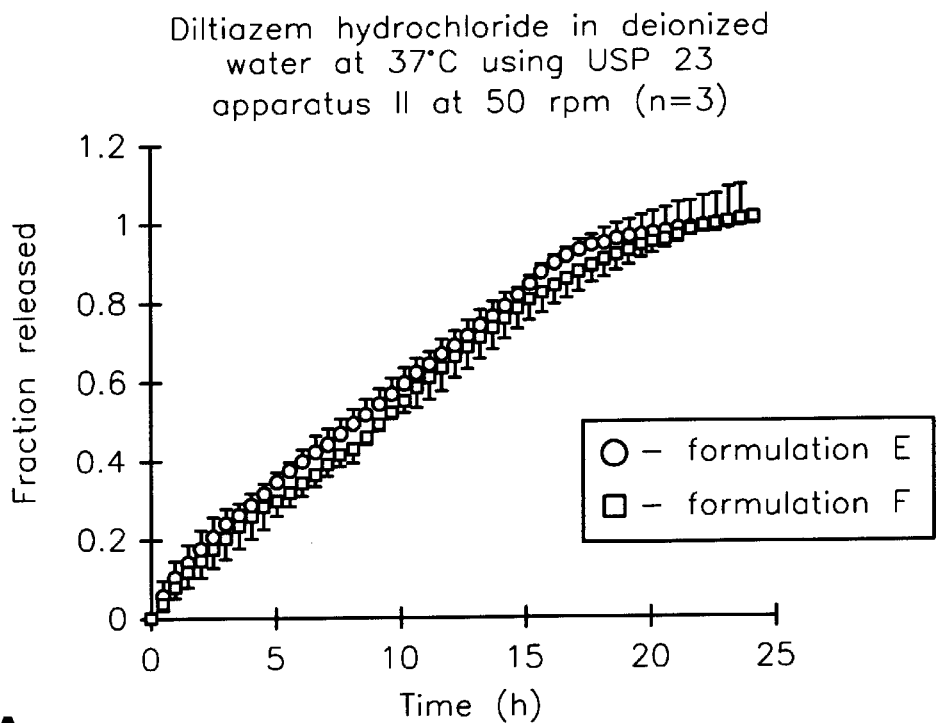
FIG. 3a is a graph showing the fraction release profile of diltiazem hydrochloride from the tablets in accordance with example 1 of the present invention and formulation E and F of Table 1.
Figure 3B:
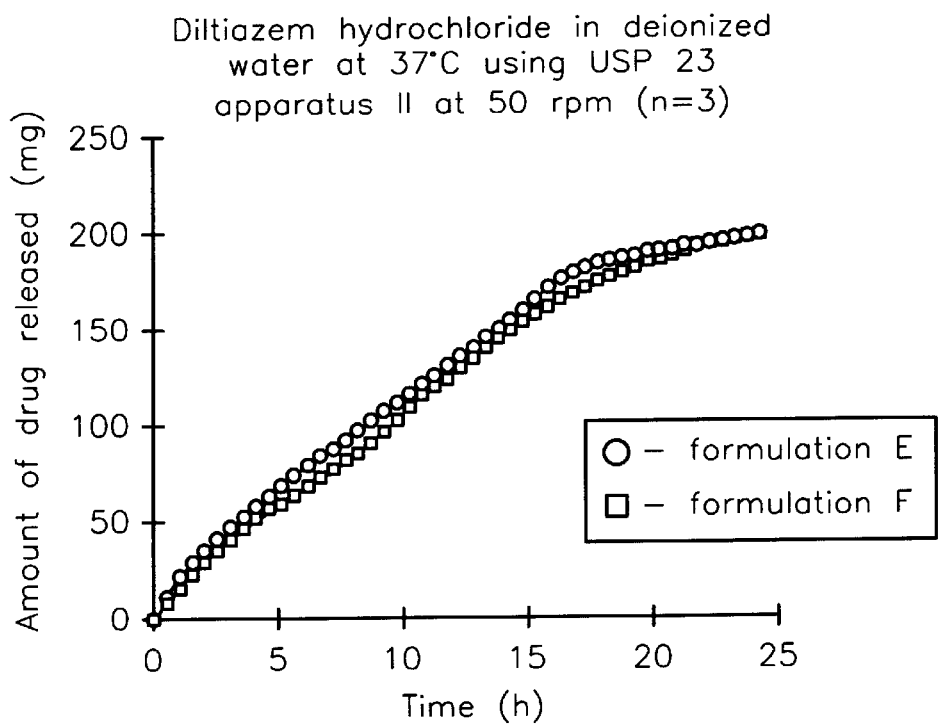
FIG. 3b is a graph showing the amount of diltiazem hydrochloride release from the tablets in accordance with example 1 of the present invention and formulation E and F of Table 1.
Figure 4A:
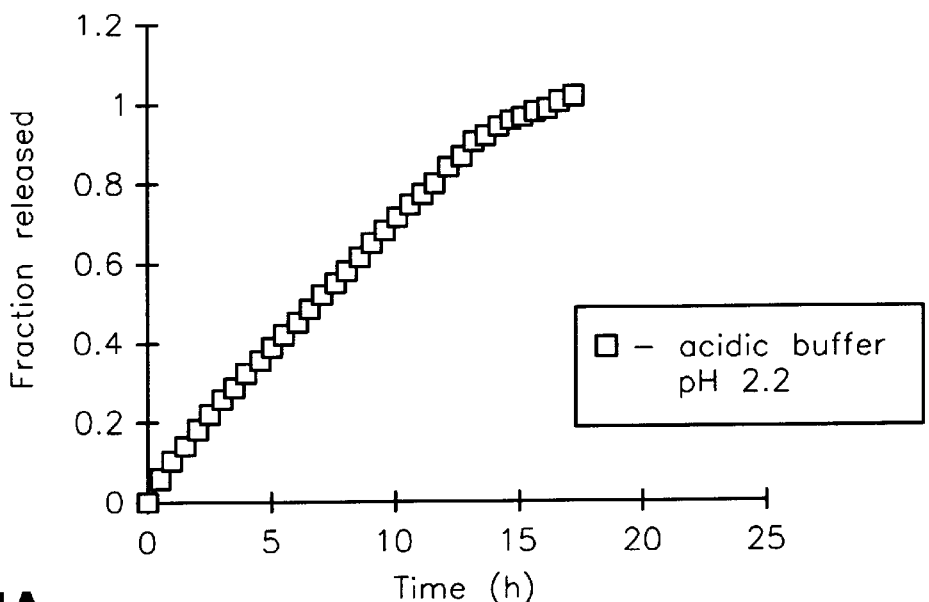
FIG. 4a is a graph showing the dissolution profile of diltiazem hydrochloride from formulation A of Table 1 in pH 2.2.
Figure 4B:
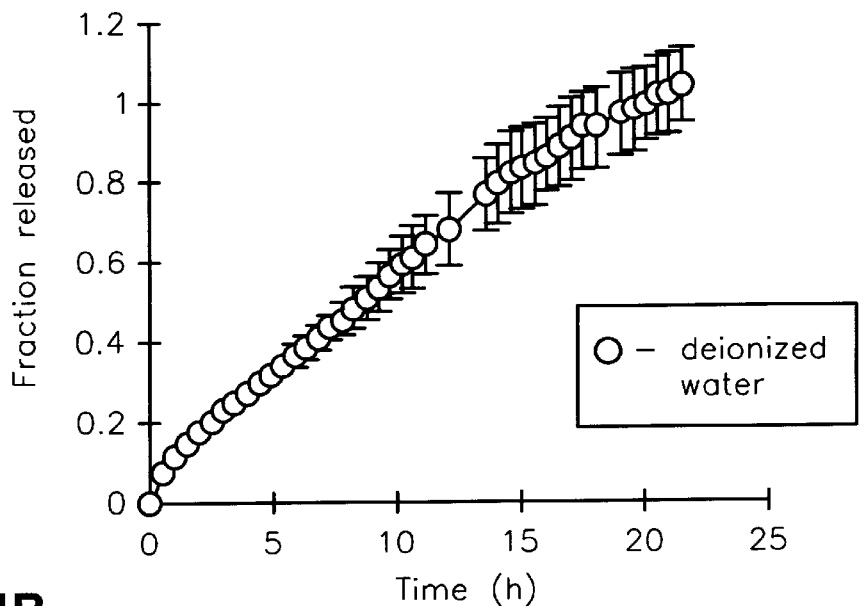
FIG. 4b is a graph showing the dissolution profile of diltiazem hydrochloride from formulation A of Table 1 in deionized water.
Figure 4C:
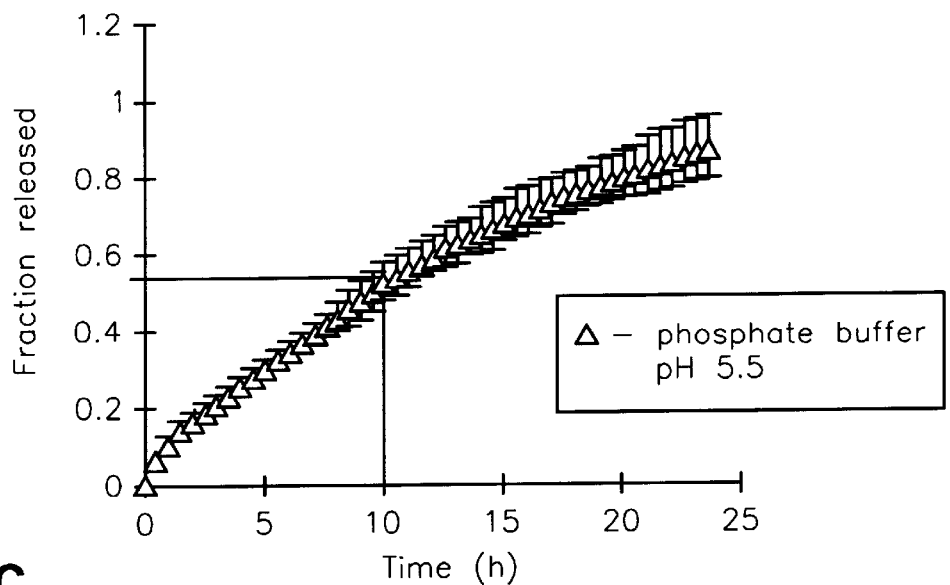
FIG. 4c is a graph showing the dissolution profile of diltiazem hydrochloride from formulation A of Table 1 in pH 5.5.
Figure 4D:
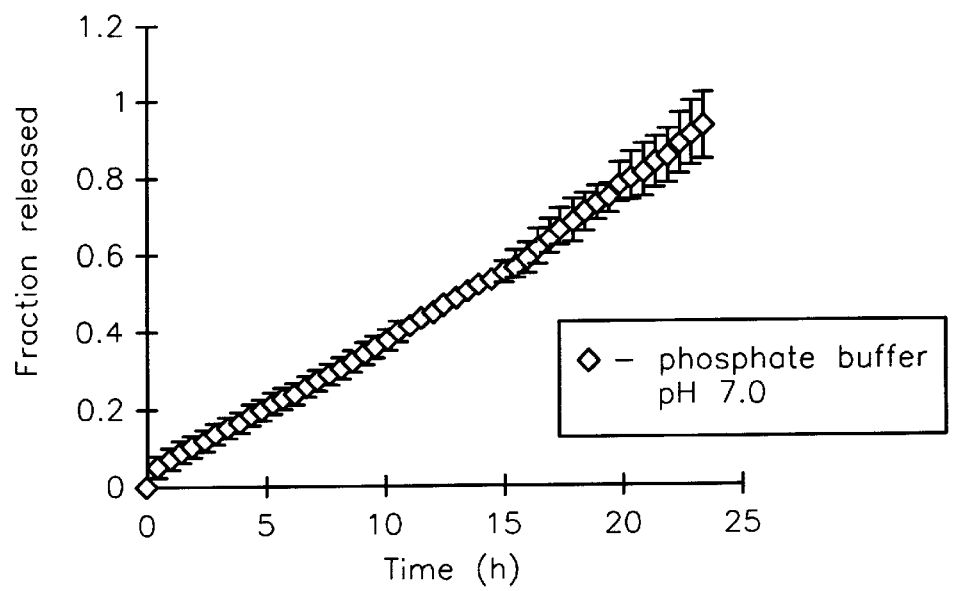
FIG. 4d is a graph showing the dissolution profile of diltiazem hydrochloride from formulation A of Table 1 in pH 7.0.
Figure 5A:
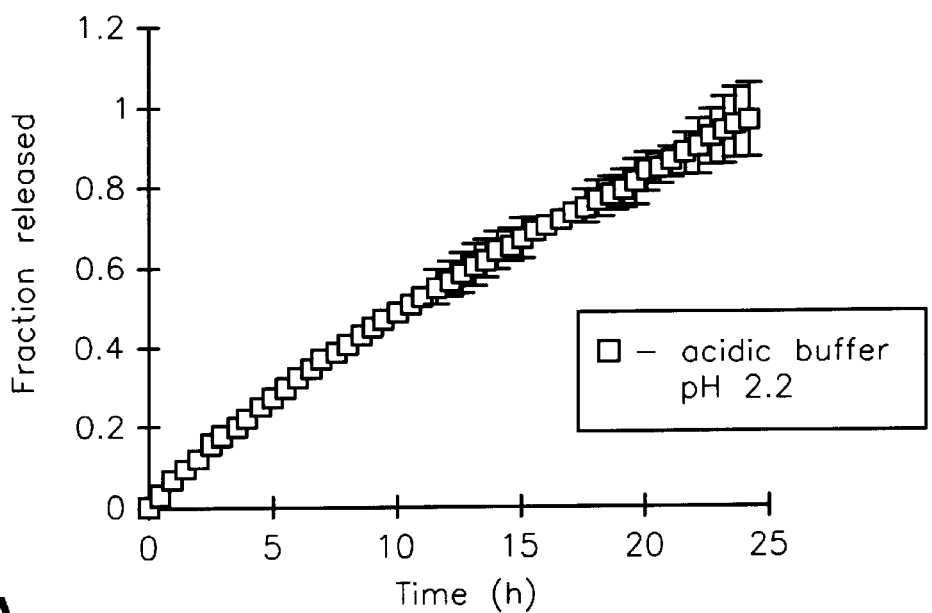
FIG. 5a is a graph showing the dissolution profile of diltiazem hydrochloride from formulation B of Table 1 in pH 2.2.
Figure 5B:
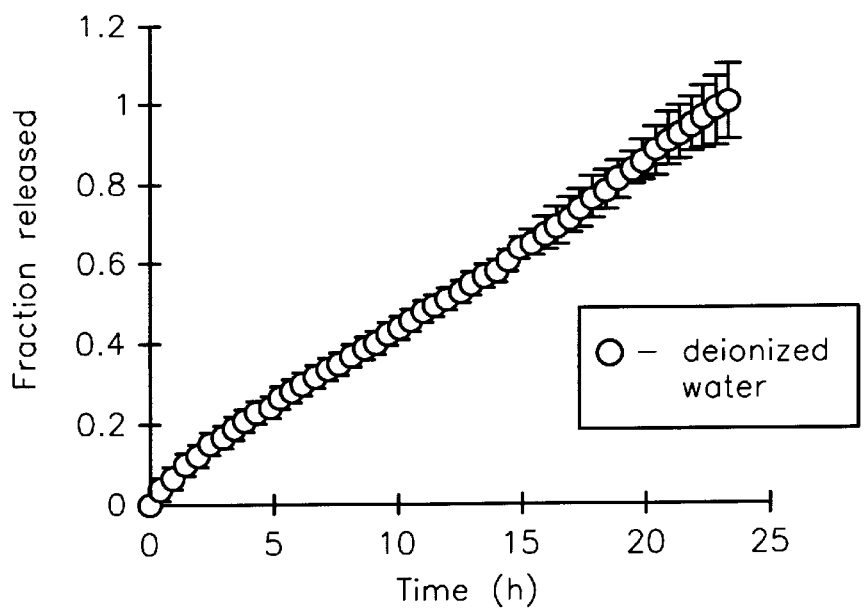
FIG. 5b is a graph showing the dissolution profile of diltiazem hydrochloride from formulation B of Table 1 in deionized water.
Figure 5C:
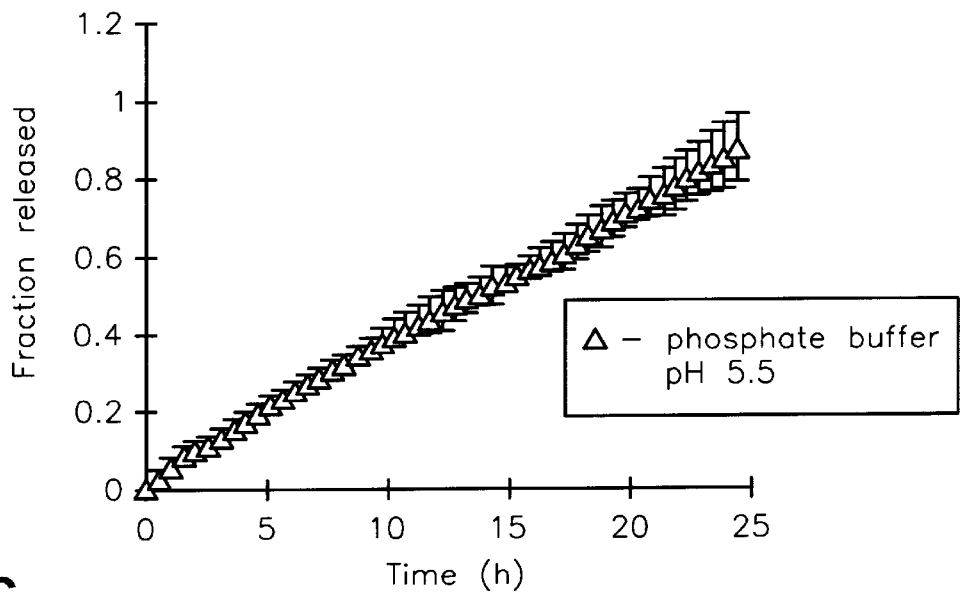
FIG. 5c is a graph showing the dissolution profile of diltiazem hydrochloride from formulation B of Table 1 in pH 5.5.
Figure 5D:
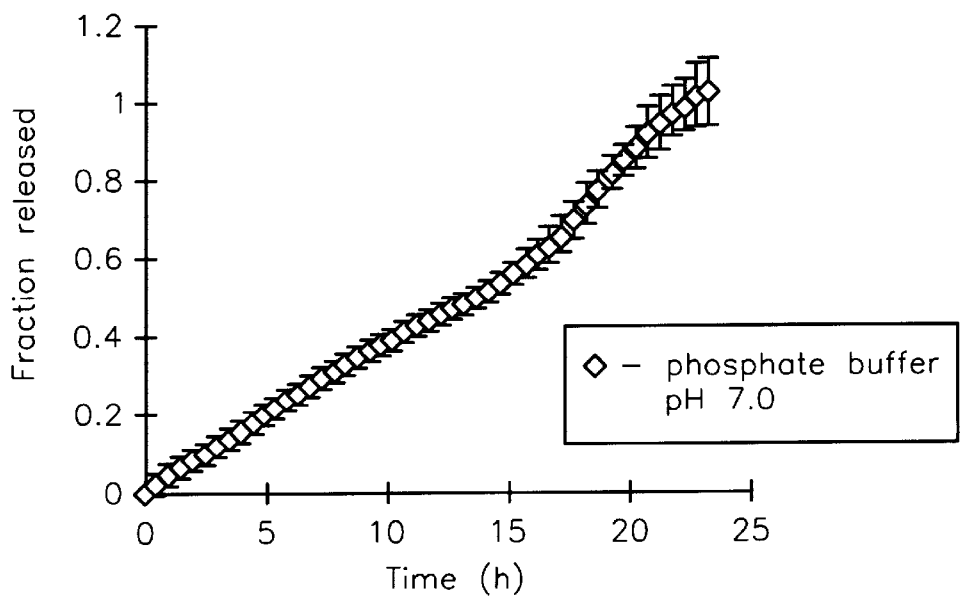
FIG. 5d is a graph showing the dissolution profile of diltiazem hydrochloride from formulation B of Table 1 in pH 7.0.

FIG. 2 shows the dissolution profile of diltiazem hydrochloride in deionized water for formulations C and D of Table 1. After an initial burst, the release of drug in formulation C is nearly linear, both in fraction released (FIG. 2a) and in actual milligrams released (FIG. 2b). The absence of pectin and gelatin in Formulation D as described in Table 1, results in a less linear release rate of drug, as seen in both FIGS. 2a and 2b. FIG. 3 is a similar dissolution profile for diltiazem, corresponding to formulations E (FIG. 3a) and F (Figure b) of Table 1. Again, the release rates of drug from the tablets are linear and relatively constant over a 19 hour time period.

FIGS. 4 and 5 show the fraction of diltiazem released from formulations A (FIG. 4) and formulation B (FIG. 5) over time under different pH conditions. Drug release in vitro should ideally be independent of variations in pH of the dissolution medium. If this were true, this would lead to a correlation between the in vitro studies and in vivo results. To measure drug release as a function of changes in dissolution media pH, dissolution studies were conducted using the tablets set forth in Table 1. As seen in both FIGS. 4 and 5, the release of pharmaceutical agent was essentially the same in pH of 2.2, 5.5, 7.0, and in deionized water. This shows that variations in pH and ionic strength did not seem to significantly affect the viscosity or release rate of the polymeric mixture (pectin:HPMC).

It should be pointed out that because pectin is an anionic polysaccharide composed of 1-4-linked α-D-galacturonic acid, its gelation is expected to be influenced by variation in pH and the ionic strength. However, pectin, an anionic material, is highly methoxylated (degree of methoxylation, ~70%) was used and no significant changes in viscosity and gelation of the pectin:HPMC mixture was evident from changes in pH, as seen in FIGS. 4 and 5. Gelation of HPMC, because it is a nonionic polymer, is independent of the pH, and HPMC constitutes a major proportion of the matrix formulation investigated in this study. In addition, the gel microstructure and its molecular organization is likely to be composed of domains of pectin and HPMC that will influence the viscoelastic behavior of the final gel and thus the diffusion/erosion process. The nature of the viscoelastic properties of the swollen gel in hydrophilic tablet matrices is naturally influenced by factors such as temperature and the presence of other formulation components (i.e., lubricant, drug-to-matrix ratio, and drug solubility).

Figure 6:
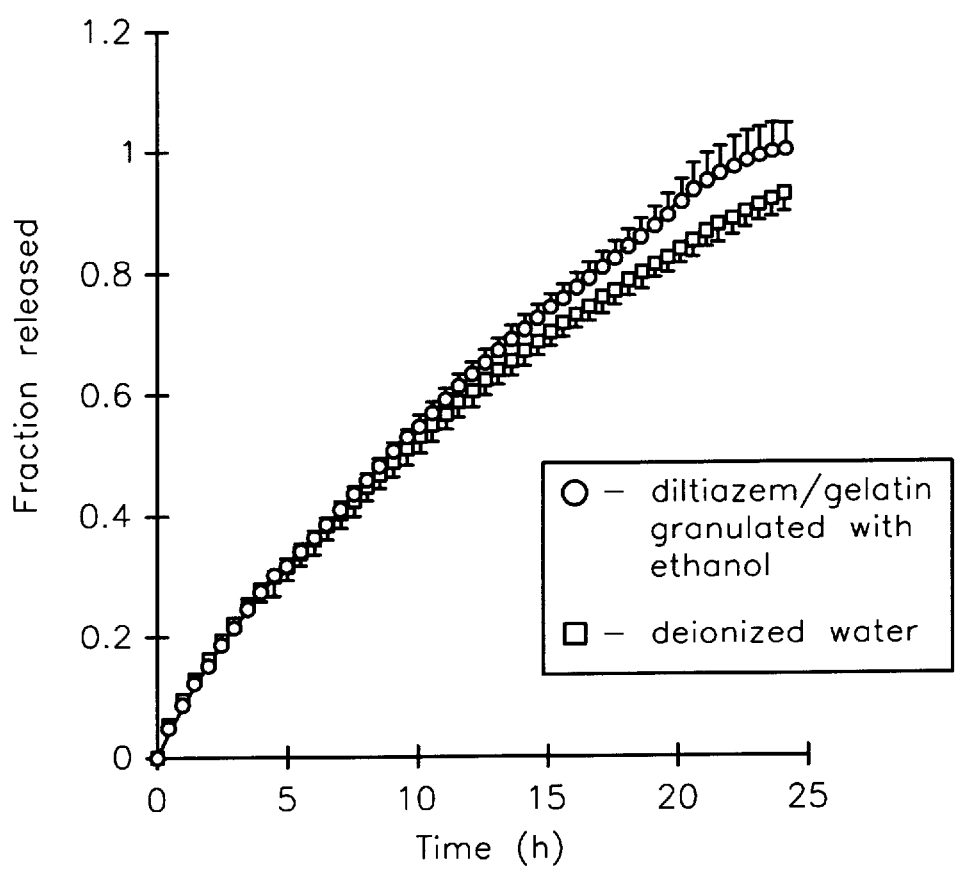
FIG. 6 is a graph showing the dissolution profile of fraction of diltiazem hydrochloride released from the tablets in accordance with example 1 is of the present invention and formulation E of Table 1, where the granulating liquid was either water or ethanol.
Figure 7:
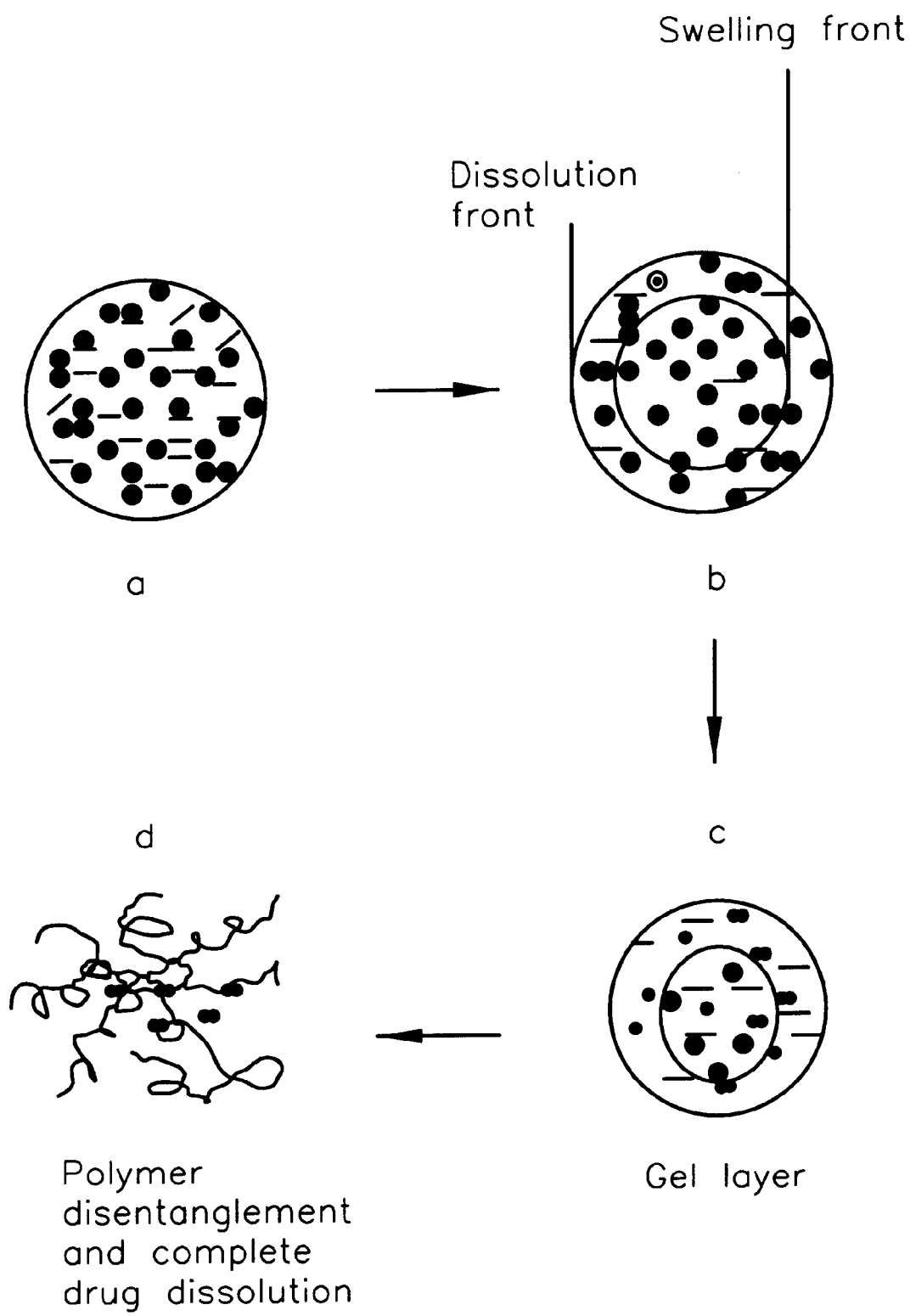
FIG. 7 is a schematic representation of drug distribution, changes in morphological dynamics and matrix swelling during dissolution study.
Figure 8A:
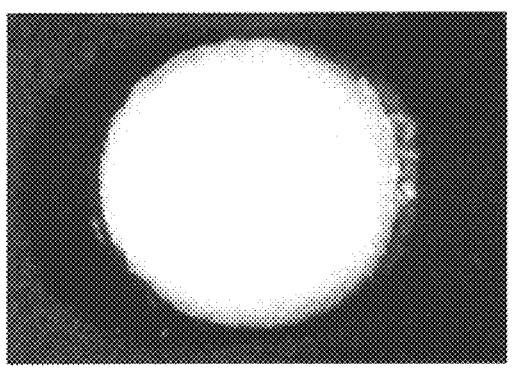
FIG. 8 are photographs showing the changes with swelling 1 to 3 hours after hydration in a formulation as otherwise exemplified in Example 1.
Figure 8B:
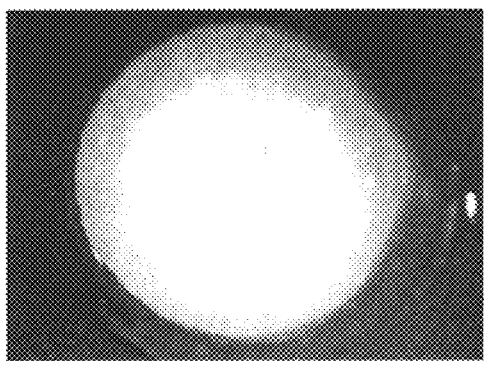
Figure 8C:
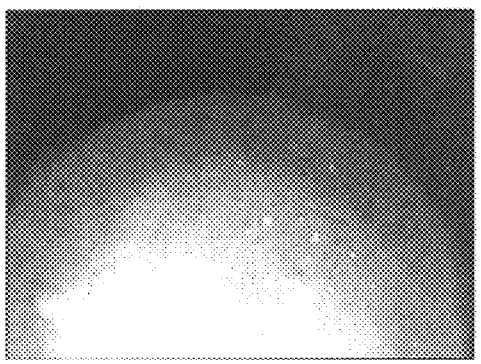
Figure 8D:
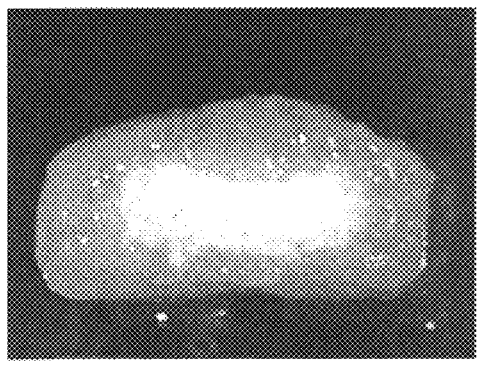

FIG. 6 shows the dissolution profile for diltiazem hydrochloride in formulation E of Table 1. It is apparent from the graph that when diltiazem and gelatin are granulated with ethanol, the fraction released is linear and nearly identical to deionized water for approximately 12 hours.

FIGS. 7a through 7d are a schematic representation of drug distribution and matrix swelling during the dissolution process (stages a–b). Water diffuses into the matrix, reaching a threshold value when the glassy matrix undergoes a phase transition to the rubbery state, (stages b–c). Drug is then released from the swollen system, which gradually erodes away and finally completely dissolves. The drug release for the linear portion is due to swelling/erosion of the pectin/HPMC-based matrix tablet, as well as the appearance of gelatin-drug particles with their own rate-limiting gel environment within different swollen boundaries. These gelatin-drug particles gradually dissolve into the matrix dissolution front (i.e., the water-gel interface) where water content is high and gel structure is relatively weak. At the interface, as the polymer concentration decreases, the gel microstructure approaches the disentanglement threshold and continuously dissolves away. As a result, the effect of increasing diffusional path length on drug release is counterbalanced by both swelling and erosion as well as the appearance of gellified drug granules at the dissolution front with linear release.

The swollen matrix gradually erodes away and completely dissolves toward the end of dissolution. The drug release for the linear portion of the release curve is ascribed to swelling/erosion of the pectin/HPMC-based matrix tablet. In addition, the appearance of gelatin-drug particles with their own rate limiting gel-environment within the swollen boundaries contributes toward this linearity by gradually dissolving into the matrix structure.

It is anticipated with swellable hydrophilic systems containing different ratios of polymeric material and a highly soluble drug, that release mechanisms will be influenced by a number of parameters. These include but are not limited to: (i) rate of fluid ingress into the matrix, (ii) rate of matrix swelling and molecular diffusion of the drug through the swollen gel layer into dissolution medium due to the chemical potential gradient, (iii) polymer relaxation and chain disentanglement which is usually associated with structural changes, stresses, phase transition from glassy to rubbery and increases in free volume, (iv) non-homogeneous gel microstructure and variation in the glass transition temperature of the matrix components (i.e., HPMC, pectin, and gelatin) as well as the existence of polymeric domains within the swollen gel, (v) processing techniques involved in tablet manufacturing, such as direct compression, granulation and solvent effect, and (vi) dissolution/erosion and total disentanglement at the dissolution front. The present invention is capable of controlling drug release rate and kinetics and can provide enhanced linearity in the release process.

FIG. 8 consists of photographs of the ternary polymeric matrix system and its dimensional changes with swelling at 1 hour (a) and 3 hours (b) after hydration. Both gel layer and glassy core as well as an anisotropic gel structure with various polymeric domains within the gel boundary are clearly evident in the magnified photographs (c) and tablet cross-section (d) taken 3 hours after hydration. As the gel-layer thickness increased and swelling progressed, a more evenly hydrated region was formed at the matrix front (i.e., the water-gel interface). In fact, where the concentrations of the polymer in the inner gel layer (i.e., close to the swelling front) is high, distinctive domains of uneven hydration related to the pectin, HPMC and drug gelatin granules around the glassy core was visually observed. These suggest that the drug transport process from the matrix is influenced by the rate of fluid ingress and drug dissolution as well as by the swelling capacities of various polymeric domains within the matrix.

Figure 9:
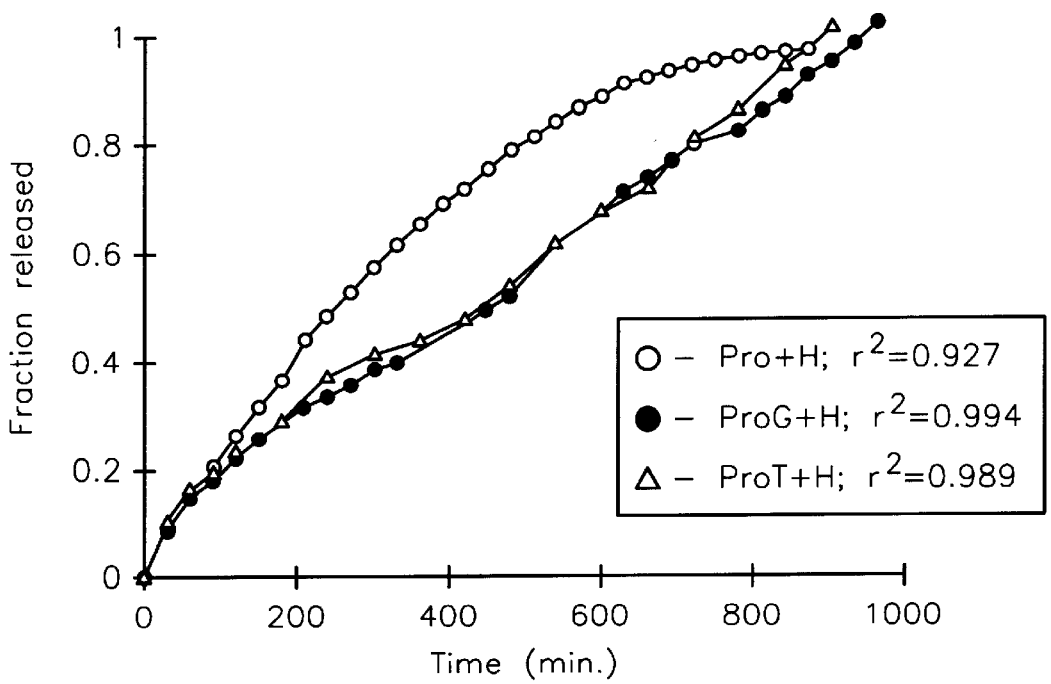
FIG. 9 is a graph showing the release profile of propranolol from the tablets in accordance with example 2 of the present invention using either gelatin or tragacanth as the gum.

FIG. 9 shows the linear release profile for propranolol of the present invention. The fraction released over time is significantly improved when gelatin or tragacanth materials have been used for drug granulation/coating and then incorporated into the binary polymeric matrix and directly compressed into a monolithic system. The correlation coefficients with gelatin (0.994) and tragacanth (0.989), shows increased linearity when compared to the coefficient of control (0.927).

Figure 10:
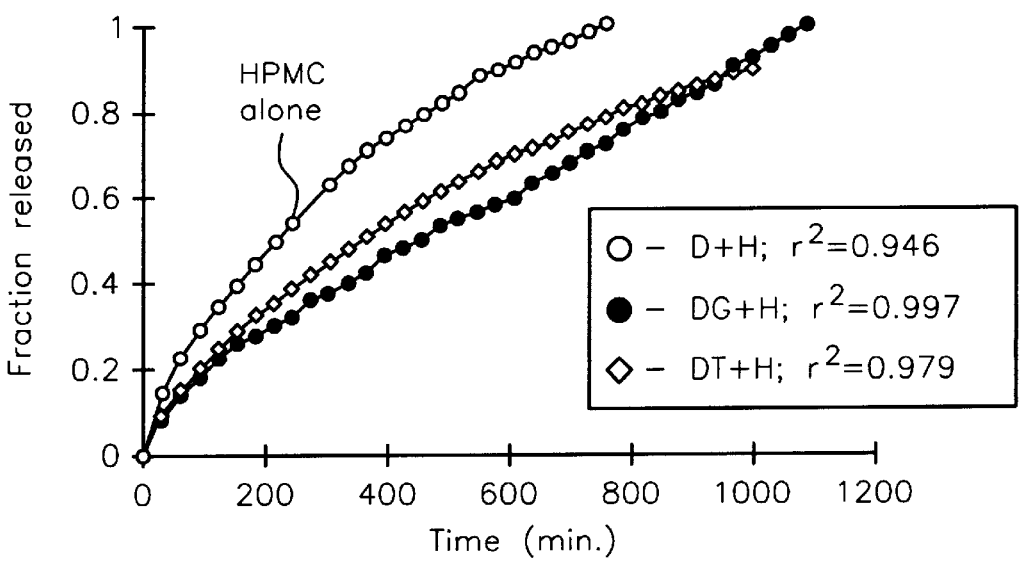
FIG. 10 is a graph showing the release profiles of diltiazem from the tablets in the presence of either gelatin or tragacanth as the gum.

FIG. 10 shows a release profile for diltiazem when gelatin and tragacanth have been used for drug granulation/coating and then incorporated into the binary polymeric matrix of the present invention. Again, the measured coefficients observed for gelatin (0.997) and tragacanth (0.979) show increased linearity when compared to the coefficient of 0.946 observed in the absence of either gelatin or tragacanth.

Figure 11:
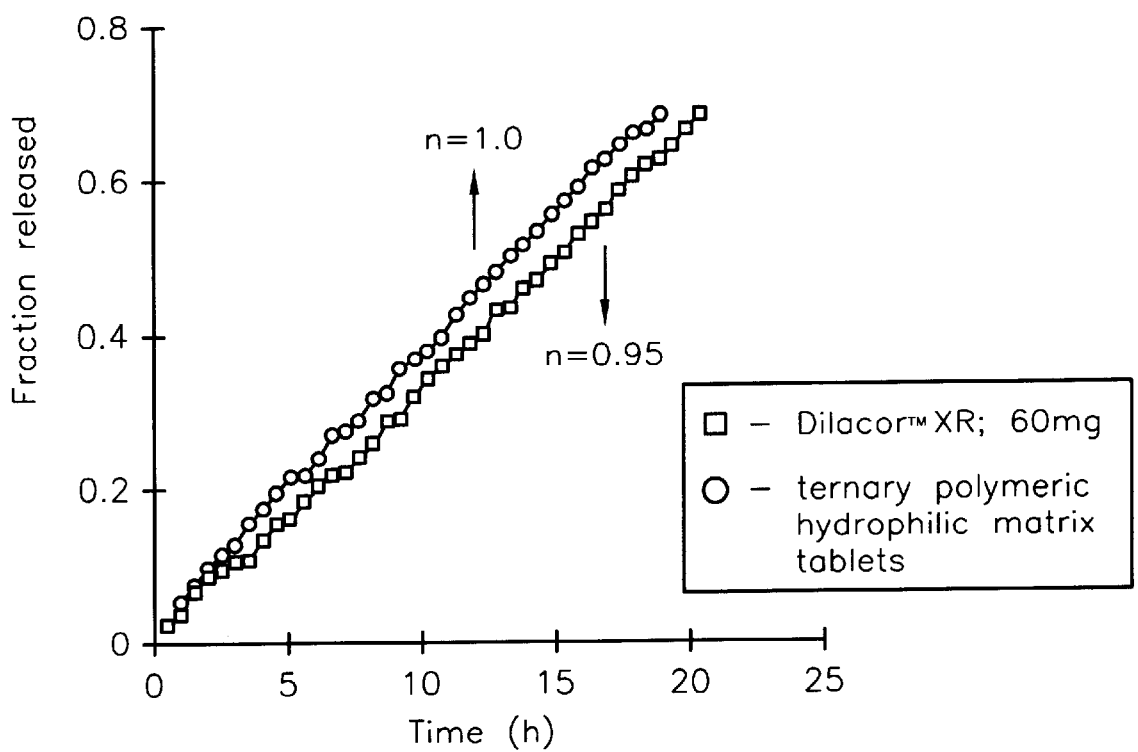
FIG. 11 is a comparison of diltiazem hydrochloride release from a commercial product and from the ternary polymeric hydrophilic matrix tablets of the present invention.

FIG. 11 is of a comparison of diltiazem hydrochloride release from a commercial product and from the ternary polymeric hydrophilic matrix tablets. All tablets tested contained 60 mg of diltiazem hydrochloride. The release profiles are very similar in terms of linearity and drug fraction released ($M_t/MA_\infty \leq 60\%$, $r^2=0.999$, confidence limit p=0.95). The calculated n values of 1.00 for the commercial product and 0.95 for the present system indicate that the release kinetics in both cases are relaxational/erosion-dependent. The simple ternary matrix system shows a slight initial burst effect followed by linear release up to 70% of the loading dose.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed:

1. A simple compressed matrix tablet suitable for manufacture on high speed tableting machines which provides sustained delivery of soluble pharmaceutical agents comprising:
   (a) a singular polymer matrix of a polymer which is swellable and erodible, and
   (b) a plurality of granules embedded within and dispersed throughout said polymer matrix, said granules comprising:
       (i) a polymer which is swellable; and
       (ii) a pharmaceutically effective amount of a soluble pharmaceutical agent incorporated in the polymer (i) of said granules,
   wherein the polymer of the matrix (a) is more swellable and erodible than the polymer (i) of said granules and wherein the polymer matrix has diffusion rate coefficient greater than the diffusion rate coefficient of said granules, the polymer of the matrix (a) is selected from the group consisting of HPMC, polyethylene oxide, and a mixture of HPMC and pectin, and the polymer (i) of the granule is selected from the group consisting of gelatin, gum tragacanth, and pectin.

2. The matrix tablet of claim 1 wherein the polymer of the matrix (a) consists of HPMC and pectin in a pectin:HPMC weight ratio in the range of 2:7 to 4:5.

3. The matrix tablet of claim 1 or 2, wherein the weight ratio of polymer (i) to soluble pharmaceutical agent is in the range of about 1:1 to about 1:5 and wherein the weight ratio of polymer (a) to said granules is in the range of about 0.68:1 to about 3.45:1.

4. A process for preparing a formulation suitable for compression into a simple compressed matrix tablet which can be manufactured on high speed tableting machines and provides sustained delivery of soluble pharmaceutical agents comprising the steps of:
   (a) granulating a soluble pharmaceutical agent with a first polymer to form a granule consisting essentially of said pharmaceutical agent and said first polymer,
   (b) blending a plurality of said granules with a second polymer to form a singular polymer matrix in which said granules are embedded and dispersed throughout,
   wherein the polymer of the matrix (a) is more swellable and erodible than the polymer (i) of said granules and wherein the polymer matrix has diffusion rate coefficient greater than the diffusion rate coefficient of said granules, the polymer of the matrix (a) is selected from the group consisting of HPMC, polyethylene oxide, and a mixture of HPMC and pectin, and the polymer (i) of the granule is selected from the group consisting of gelatin, gum tragacanth, and pectin.

5. The process of claim 4, wherein the weight ratio of said first polymer to soluble pharmaceutical agent is in the range of about 1:1 to about 1:5 and wherein the weight ratio of said second polymer to said granules is in the range of about 0.68:1 to about 3.45:1.

6. A tablet according to claim 1, wherein said pharmaceutical agent is diltiazem.

7. A tablet according to claim 1, wherein said pharmaceutical agent is propranolol.

8. The simple compressed matrix tablet of claim 1 in which release occurs over an extended period of time of at least 12 hours.

9. The simple compressed matrix tablet of claim 8 in which release occurs over an extended period of time of about 16 to about 20 hours.

10. The matrix tablet according to claim 9 comprising a soluble pharmaceutical agent selected from the group consisting of diltiazem and propanolol.

* * * * *